United States Patent [19]

Sikorski et al.

[11] Patent Number: 4,519,832

[45] Date of Patent: May 28, 1985

[54] UNSYMMETRICAL AMINOSULFINAMIDE DERIVATIVES OF N-PHOSPHONOMETHYLGLYCINE TRIESTERS, HERBICIDAL COMPOSITIONS AND USE

[75] Inventors: James A. Sikorski, Kirkwood; Mary A. Hoobler, Olivette, both of Mo.

[73] Assignee: Monsanto Company, St. Louis, Mo.

[21] Appl. No.: 605,003

[22] Filed: Apr. 27, 1984

[51] Int. Cl.$^3$ .................. C07F 9/40; A01N 57/20; A01N 57/24

[52] U.S. Cl. .................................. 71/87; 544/57; 544/157; 546/22; 260/239 BF; 260/941; 260/944

[58] Field of Search .............. 260/941, 944, 239 BF; 71/87; 544/57, 157; 546/22; 564/100, 102

[56] References Cited

U.S. PATENT DOCUMENTS 4,120,689 10/1978 Dutra ............................ 71/86
4,405,356 9/1983 Sikorski et al. ................. 71/87
4,445,928 5/1984 Sikorski et al. ................. 71/87

FOREIGN PATENT DOCUMENTS 156295 12/1981 Japan .
120595 7/1982 Japan .
222096 12/1983 Japan .

OTHER PUBLICATIONS

Hoobler et al., *Chemical Abstracts*, vol. 99, (1983), No. 6049p, Belgian Pat. No. 894,595.

*Primary Examiner*—Robert W. Ramsuer
*Attorney, Agent, or Firm*—Raymond C. Loyer; Richard H. Shear; Arnold H. Cole

[57] ABSTRACT

This invention relates to unsymmetrical aminosulfinamide derivatives of N-phosphonomethyl-glycine triesters which are useful as herbicides. This invention further relates to herbicidal compositions containing such derivatives and to herbicidal methods employing such compounds and compositions.

30 Claims, No Drawings 4,519,832

UNSYMMETRICAL AMINOSULFINAMIDE DERIVATIVES OF N-PHOSPHONOMETHYLGLYCINE TRIESTERS, HERBICIDAL COMPOSITIONS AND USE

This invention relates to unsymmetrical aminosulfinamide derivatives of N-phosphonomethylglycine triesters which are useful as herbicides. This invention further relates to herbicidal compositions containing such derivatives and to herbicidal methods employing such compounds and compositions.

BACKGROUND OF THE INVENTION

U.S. Pat. No. 4,120,689 issued to Gerard A. Dutra on Oct. 17, 1978, describes alkyl-[di(benzyl) or di(aryl)]esters of N-phosphonomethylglycine which are produced by the reaction of a dibenzyl or diaryl phosphite with an N-methylene alkyl glycinate trimer. These esters and the hydrolysis products thereof containing at least one benzyloxy or aryloxy group bonded to phosphorus are compounds disclosed as having the formula

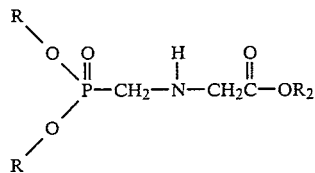

wherein R is a member of the group consisting of phenyl, benzyl, naphthyl, biphenylyl, and phenyl, benzyl or naphthyl groups substituted with from 1 to 3 groups selected from the class consisting of hydroxyl, lower alkyl, lower alkoxy, lower alkylthio, trifluoromethyl, carbo(lower alkoxy), nitro or halo; $R_1$ is hydrogen or an R group, and $R_2$ is a lower alkyl group or hydrogen, and the strong acid salts of the compounds wherein neither $R_1$ or $R_2$ is H. The aforementioned compounds are disclosed as useful as post-emergent herbicides.

U.S. Pat. No. 4,405,356 issued to James A. Sikorski et al on Sept. 20, 1983, discloses compounds represented by the formula

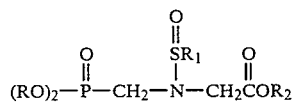

wherein R is selected from the group consisting of phenyl, naphthyl, or biphenylyl; or phenyl, naphthyl, or biphenylyl substituted with from 1 to 3 substituents independently selected from the group consisting of hydrogen, lower alkyl, lower alkoxy, methylenedioxy; $R_1$ is independently phenyl or phenyl substituted with from one to three substituents selected from the group consisting of lower alkyl, lower alkoxy, halogen, trifluoromethyl, cyano, nitro, and halogen and wherein $R_2$ is lower alkyl or araloweralkyl.

Belgian Pat. No. 894,595 issued to James A. Sikorski et al on Apr. 5, 1983, discloses compounds represented by the formula

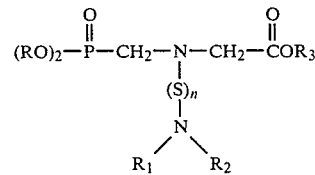

wherein n is an integer 1 or 2 and wherein R is selected from the group consisting of phenyl, naphthyl, or biphenylyl; or phenyl, naphthyl, or biphenylyl substituted with from 1 to 3 substituents independently selected from the group consisting of lowr alkyl, lower alkoxy, lower alkylthio, alkoxycarbonyl, methylenedioxy, trifluoromethyl, cyano, nitro, and halogen; and wherein $R_1$ and $R_2$ are independently selected from the group consisting of hydrogen, cycloalkyl, alkyl, alkyl substituted with 1 or 2 substituents independently selected from the group consisting of lower alkoxy, lower alkylthio, cyano, lower alkoxycarbonyl, bis(aryloxy)phosphinyl wherein said aryl portion thereof corresponds to a group selected from R; phenyl or phenyl substituted with 1 or 2 substituents independently selected from the group consisting of lower alkyl and lower alkoxy; acyl or aroyl; or $R_1$ and $R_2$ are independently selected from the aforerecited groups and joined together to form a cyclic structure having 3–8 atoms therein and $R_3$ is lower alkyl or aralower alkyl.

Japanese L.O.P. No. 56-156295/1981 describes the preparation and herbicidal utility of symmetrical aminosulfinamide derivatives of the formula

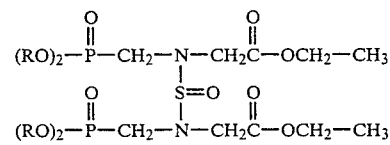

wherein R represents phenyl which are useful as herbicides.

BRIEF SUMMARY OF THE INVENTION

In accordance with the present invention there is provided novel aminosulfinamide derivatives of N-phosphonomethylglycine triesters represented by the formula

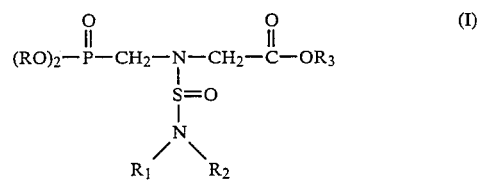

wherein R is selected from the group consisting of phenyl; or phenyl substituted with from 1 to 3 substituents independently selected from the group consisting of lower alkyl, lower alkoxy, trifluoromethyl, nitro, and halogen; and wherein $R_1$ and $R_2$ are independently selected from the group consisting of alkyl, cycloalkyl, alkenyl, alkynyl, aralkyl and R; or $R_1$ and $R_2$ are independently selected from the aforerecited groups and joined together through the nitrogen to form a cyclic structure having 4 to 8 atoms therein and $R_3$ is lower alkyl or aralower alkyl. The above described compounds are herbicidally active.

DETAILED DESCRIPTION OF THE INVENTION

These compounds are prepared by reacting a compound of the formula

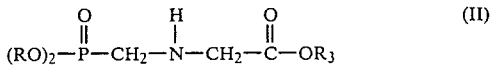

$$(RO)_2-\overset{O}{\underset{\|}{P}}-CH_2-\overset{H}{\underset{|}{N}}-CH_2-\overset{O}{\underset{\|}{C}}-OR_3 \qquad (II)$$

wherein R and $R_3$ are as aforedefined with thionyl chloride in an aprotic solvent and in the presence of a hydrogen chloride acceptor to form a compound of the formula

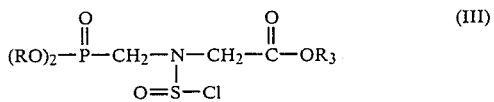

$$(RO)_2-\overset{O}{\underset{\|}{P}}-CH_2-\underset{\underset{O=S-Cl}{|}}{N}-CH_2-\overset{O}{\underset{\|}{C}}-OR_3 \qquad (III)$$

wherein R and $R_3$ are as aforedefined.

The reaction temperature for the aforerecited reaction is in the range from about $-50°$ C. to about $100°$ C., and is preferably from about $-30°$ C. to about $+30°$ C., although greater or lower temperatures may be employed if desired.

In preparing the compounds of Formula (III), the ratio of reactants of Formula (II) and thionyl chloride is not narrowly critical. For best results, however, for each mole of a compound of Formula (II), one should employ one mole of thionyl chloride to produce one mole of a compound of Formula (III).

The compound of Formula (III) is reacted with a suitable secondary amine of the Formula

$$\underset{R_2}{\overset{R_1}{\diagdown}}N-H \qquad (IV)$$

wherein $R_1$ and $R_2$ are as aforedefined in an aprotic solvent and in the presence of a hydrogen chloride acceptor to form a compound of Formula (I).

In reacting a compound of Formula (III) with a compound of Formula (IV), the temperature is in the range from about $-50°$ C. to about $100°$ C. and is preferably from about $-30°$ C. to about $+30°$ C. although greater or lower temperatures may be employed if desired.

The ratio of compounds of Formula (III) to compound of Formula (IV) is not critical. For best results, however, one should employ for each mole of a compound of Formula (III) a mole of a compound of Formula (IV).

Typical compounds which may be employed as a compound of Formula (IV) include symmetrical secondary amines such as dimethylamine; diethylamine, diisopropylamine, diallylamine, dibutylamine, dioctylamine, diphenylamine, dicyclohexylamine, dibenzylamine, dipropargylamine, piperidine, homopiperidine, or morpholine and the like or unsymmetrical secondary amines such as N-methylaniline, N-methylbenzylamine, N-methylcyclohexylamine, N-methylbutylamine, N-methylpropargylamine and the like.

It is preferred that R is phenyl, $R_1$ and $R_2$ are preferably alkyl such as methyl, benzyl, phenyl or cyclic such as morpholino. These compounds appear to be most active herbicidally.

Illustrative of the substituted phenyl groups which R, $R_1$, and $R_2$ independently represent are mono-substituted phenyl wherein the substituent is in the ortho, meta or para position, for example, methylphenyl, butylphenyl, methoxyphenyl, butoxyphenyl, fluorophenyl, chlorophenyl, bromophenyl, iodophenyl, trifluoromethylphenyl, nitrophenyl and the like, and the di- and trisubstituted phenyl groups wherein the substituents are the same or different and are located in the 2, 3, 4, 5, or 6 positions of the phenyl ring, for example, dichlorophenyl, dimethylphenyl, methylchlorophenyl, ethylfluorophenyl, dibutoxyphenyl, butylnitrophenyl, trimethylphenyl, trichlorophenyl, tributylphenyl, ethyldichlorophenyl and the like.

The term "alkyl" is employed throughout the claims and description to mean a substituted or unsubstituted monovalent radical in a straight or branched chain of the formula $C_nH_{2n+1}$-derived from an aliphatic hydrocarbon by removal of one hydrogen therefrom wherein n is an integer from 1 to 10.

As employed herein, the term "lower alkyl" designates alkyl radicals which have from 1 to 4 carbon atoms in a straight or branched chain, for example, methyl, ethyl, propyl, isopropyl, butyl, isobutyl, sec-butyl, and t-butyl.

The term "halo" or "halogen" as employed herein means chlorine, bromine, iodine, and fluorine.

The term "lower alkoxy" includes groups representative of the term "lower alkyl" in combination with oxygen and includes methoxy, ethoxy, propoxy, butoxy, mixtures thereof and the like.

Typical groups representative of the term "alkenyl" includes groups representative of the term "alkyl" which also contains a carbon-carbon double bond and includes allyl, propenyl, butenyl and the like.

Typical groups representative of the term "alkyl" includes groups representative of the term "lower alkyl" as well as groups such as n-pentyl, n-hexyl, n-heptyl, n-octyl, isopentyl, neopentyl, isohexyl, 2-methylpentyl, 2,2-dimethylbutyl, 2,3-dimethylbutyl and the like.

The term "aralkyl" includes groups representative of the term "alkyl" in combination with phenyl or substituted phenyl groups and includes benzyl, phenethyl, phenylbutyl, and the like.

The term "cycloalkyl" is employed throughout the claims and description to mean carbon and hydrogen atoms arranged in a cyclic or ring arrangement having 3 to 8 carbon atoms therein. Typical groups representative of the term "cycloalkyl" include cyclopentyl, cyclohexyl, cyclopropyl, cyclooctyl and the like.

Typical groups representative of the embodiment wherein $R_1$ and $R_2$ are joined together to form a cyclic arrangement include morpholino, piperidino, thiomorpholino, azepano and the like.

Typical groups representative of the term "alkynyl" include groups representative of the term "alkyl" which also contain a carbon-carbon triple bond and include propargyl and butynyl and the like.

The hydrogen chloride acceptor is typically an amine, preferably a tertiary amine which will not react with the reactants employed or products formed. Examples of suitable tertiary amine hydrogen chloride acceptors include trimethylamine, triethylamine, tributylamine, trihexylamine, 1,5-diazabicyclo-[5.4.0]-undec-5-ene, pyridine, quinoline, mixtures thereof and the like.

Due to the reactive nature of the various reaction intermediates and reactants, the process of the present invention should be conducted in an aprotic solvent under essentially anhydrous conditions. Illustrative of the aprotic solvents employed in the process of this invention include benzene, toluene, methylene chloride, tetrahydrofuran, cyclohexane, methylcyclohexane, hexane, octane, dioxane, ethyl ether, mixtures thereof and the like, although a solvent is not required.

The following illustrative, non-limiting examples will serve to further demonstrate to those skilled in the art the process of this invention wherein specific compounds within the scope of this invention can be prepared. In the examples, all parts are parts by weight unless otherwise expressly stated.

EXAMPLE 1

Preparation of Glycine, N-[chlorosulfinyl]-N-[(diphenoxyphosphinyl)methyl]-, phenylmethyl ester A methylene chloride solution of this reagent was generated using a procedure similar to that described in Japanese L.O.P 57-120595/1982 as follows:

To a flame-dried 250 ml flask, cooled under nitrogen, was added 1.46 ml (2.4 g, 0.02 mole) of thionyl chloride and 50 ml of methylene chloride. The resulting solution was cooled to $-30°$ C. and then a solution of 8.2 g (0.02 mol) of glycine, N-[(diphenoxyphosphinyl)methyl]-, phenylmethyl ester and triethylamine (2.0 g, 0.02 mole) in 50 ml of $CH_2Cl_2$ was added under nitrogen via double-ended needle at such a rate that the temperature did not exceed $-30°$ C. After 15 minutes at $-30°$ C., $^{31}P$ NMR indicated the complete consumption of the triester starting material and concomitant formation of the desired aminosulfinyl chloride intermediate ($\delta 11.0$ ppm). The resulting heterogeneous mixture was subsequently used immediately without further purification.

General Procedure for the Preparation of Unsymmetrical Aminosulfinamide Derivatives of N-Phosphonomethylglycine Triesters To a flame-dried 500 ml flask, cooled under nitrogen, was added 75 ml of $CH_2Cl_2$, 2.8 ml of triethylamine (2.0 g, 0.02 mole) and 0.02 mole of the appropriate secondary amine. The resulting solution was cooled to $-30°$ C. and then a methylene chloride solution containing glycine, N-[chlorosulfinyl]-N-[(diphenoxyphosphinyl)methyl]-, phenylmethyl ester (0.02 mole), generated as described above, was added slowly under nitrogen via double-ended needle at such a rate that the temperature did not exceed $-30°$ C. When the addition was complete, the reaction mixture was allowed to come to room temperature and then concentrated to dryness using a rotovap. The resulting residue was partitioned between diethyl ether and cold 5% aqueous NaOH. The ether layer was separated, washed successively with an equal volume of cold 5% NaOH, and then saturated aqueous NaCl, separated, dried over $MgSO_4$, filtered and concentrated to give crude products. The crude products were purified either by crystallization from 10:90 ethylacetate/cyclohexane or by preparative thin-layer chromatography on silica gel eluting with 50:50 or 30:70 ethylacetate/cyclohexane to give the desired unsymmetrical aminosulfinamide derivatives. $^1H$ and $^{31}P$ NMR, TLC and elemental analyses were all consistent with pure product.

EXAMPLE 2

Glycine, N-[(diallylamino)sulfinyl]-N-[(diphenoxyphosphinyl)methyl]-, phenylmethyl ester Glycine, N-[(diallylamino)sulfinyl]-N-[(diphenoxyphosphinyl)methyl]-, phenylmethyl ester corresponding to a compound of Formula I wherein R is phenyl, $R_1$ and $R_2$ are each allyl, and $R_3$ is benzyl; was prepared via the above procedure as a yellow oil having a refractive index $n_D^{21.7} = 1.5532$.

Anal. Calc'd. for $C_{28}H_{31}N_2O_6P_1S_1$: C, 60.64; H, 5.63; N, 5.05; S, 5.78 Found: C, 60.77; H, 5.61; N, 4.80; S, 5.60

EXAMPLE 3

Glycine-, N-[(4-morpholino)sulfinyl]-N-[(diphenoxyphosphinyl)methyl]-, phenylmethyl ester Glycine, N-[(4-morpholino)sulfinyl]-N-[(diphenoxyphosphinyl)methyl]-, phenylmethyl ester corresponding to a compound of Formula I wherein R is phenyl, $R_1$ and $R_2$ are joined together to form the cyclic structure morpholine, and $R_3$ is benzyl; was prepared via the above procedure as a yellow oil having a refractive index $n_D^{21.8} = 1.5659$.

Anal. Calc'd. for $C_{26}H_{29}N_2O_7P_1S_1$: C, 57.35; H, 5.37; N, 5.14; S, 5.89 Found: C, 57.68; H, 5.27; N, 4.82; S, 5.89

EXAMPLE 4

Glycine, N-[(dicyclohexylamino)sulfinyl]-N-[(diphenoxyphosphinyl)methyl]-, phenylmethyl ester Glycine, N-[(dicyclohexylamino)sulfinyl]-N-[(diphenoxyphosphinyl)methyl]-, phenylmethyl ester corresponding to a compound of Formula I wherein R is phenyl, $R_1$ and $R_2$ are each cyclohexyl, and $R_3$ is benzyl; was prepared via the above procedure as a white solid having a melting point of 104° C.

Anal. Calc'd. for $C_{34}H_{43}N_2O_6P_1S_1$: C, 63.93; H, 6.79; N, 4.39; S, 5.02 Found: C, 64.15; H, 6.91; N, 4.73; S, 5.16

EXAMPLE 5

Glycine, N-{[(N-methyl-N-phenyl)amino]sulfinyl}-N-[(diphenoxyphosphinyl)methyl]-, phenylmethyl ester Glycine, N-{[(N-methyl-N-phenyl)amino-sulfinyl}-N-[(diphenoxyphosphinyl)methyl]-, phenylmethyl ester corresponding to a compound of Formula I wherein R is phenyl, $R_1$ is methyl, $R_2$ is phenyl, and $R_3$ is benzyl; was prepared via the above procedure as a yellow oil having a refractive index of $n_D^{22.3} = 1.5762$.

Anal. Calc'd. for $C_{29}H_{29}N_2O_6P_1S_1$: C, 61.69; H, 5.18; N, 4.96; S, 5.68 Found: C, 61.65; H, 5.48; N, 4.87; S, 5.56

EXAMPLE 6

Glycine, N-{[(N-methyl-N-benzyl)amino]sulfinyl}-N-[(diphenoxyphosphinyl)methyl]-, methyl ester A methylene chloride solution containing glycine, N-[chlorosulfinyl]-N-[(diphenoxyphosphinyl)methyl]-, methyl ester was prepared by adding 2.4 ml (3.90 g, 0.033 mol) of thionyl chloride and 75 ml of $CH_2Cl_2$ to a flame-dried 250 ml flask, cooled under nitrogen. The resulting solution was cooled to $-30°$ C. and then a solution of 11.0 g (0.033 mol) of glycine, N-[(diphenoxyphosphinyl)methyl]-, methyl ester and 3.3 g (0.033 mol)

of triethylamine in 30 ml of $CH_2Cl_2$ was added under nitrogen via double-ended needle at such a rate that the temperature did not exceed $-30°$ C. After 15 minutes at $-30°$ C., $^{31}P$ NMR indicated the complete consumption of the triester starting material and concomitant formation of the desired aminosulfinyl chloride intermediate ($\delta 11.0$ ppm). The resulting cold, heterogeneous mixture was added via double-ended needle under nitrogen to a cold ($-30°$ C.) solution of 4.26 ml (4.0 g, 0.033 mol) of N-methylbenzylamine and 4.60 ml (3.3 g, 0.033 mol) of triethylamine in 75 ml of $CH_2Cl_2$ at such a rate that the reaction temperature did not exceed $-30°$ C. When the addition was complete, the reaction mixture was allowed to come to room temperature and was then washed successively twice with an equal volume of cold 5% aqueous NaOH, and saturated aqueous NaCl. The organic layer was separated, dried over $MgSO_4$, filtered and concentrated to give a yellow oil which was purified by preparative thin-layer chromotography on silica gel eluting with 50:50 ethyl acetate/cyclohexane to give glycine, N-{[(N-methyl-N-benzyl)amino]sulfinyl}-N-[(diphenoxyphosphinyl)-methyl]-, methyl ester corresponding to a compound of Formula I wherein R is phenyl, $R_1$ is methyl, $R_2$ is benzyl, and $R_3$ is methyl; as a yellow oil having a refractive index of $n_D^{22.8} = 1.5606$.

Anal. Calc'd. for $C_{24}H_{27}N_2O_6P_1S_1$: C, 57.36; H, 5.42; N, 5.57; S, 6.38 Found: C, 57.50; H, 5.38; N, 5.49; S, 6.34

Other compounds which may be prepared by this procedure include, but are not limited to the following:

(a) Glycine, N-[(1-piperidinyl)sulfinyl]-N-{[bis(2-methoxyphenoxy)phosphinyl]methyl}-, methyl ester.

(b) Glycine, N-{[(N-methyl-N-propargyl)-amino]sulfinyl}-N-[bis(4-chloro-3-methylphenoxy)-phosphinyl]-methyl}-, ethyl ester.

(c) Glycine, N-{[(N-methyl-N-(o-nitrophenyl))amino]sulfinyl}-N-[(diphenoxyphosphinyl)-methyl]-, phenylmethyl ester.

(d) Glycine, N-{[(N-methyl-N-(p-chlorophenyl))amino]sulfinyl}-N-[(diphenoxyphosphinyl)-methyl]-, phenylmethyl ester.

EXAMPLE 7

The post-emergence herbicidal activity of some of the various compounds of this invention was demonstrated by greenhouse testing in the following manner. A good grade of top soil is placed in aluminum pans having holes in the bottom and compacted to a depth of 0.95 to 1.27 cm. from the top of the pan. A predetermined number of seeds of each of several dicotyledonous and monocotyledonous annual plant species and/or vegetative propagules for the perennial plant species are placed on the soil and pressed into the soil surface. The seeds and/or vegetative propagules are covered with soil and leveled. The pans are then placed on a sand bench in the greenhouse and watered from below as needed. After the plants reach the desired age (two to three weeks), each pan, except for the control pans, is removed individually to a spraying chamber and sprayed by means of an atomizer operating at a positive air pressure of approximately 1.46 $kg/cm^2$ absolute. The atomizer contains 6 ml of a solution or suspension of the chemical. In that 6 ml is an amount of a cyclohexanone emulsifying agent mixture to give a spray solution or suspension which contains about 0.4% by weight of the emulsifier. The spray solution or suspension contains a sufficient amount of the candidate chemical in order to give application rates corresponding to those set forth in the tables. The spray solution is prepared by taking an aliquot of a 1.0% by weight stock solution or suspension of the candidate chemical in an organic solvent such as acetone or tetrahydrofuran or in water. The emulsifying agent employed is a mixture comprising 35 weight percent butylamine dodecylbenzene sulfonate and 65 weight percent of a tall oil ethylene oxide condensate having about 11 moles of ethylene oxide per mole of tall oil. The pans are returned to the greenhouse and watered as before and the injury to the plants as compared to the control is observed at approximately two weeks and the results recorded. The test results are reported in Table I below.

The post-emergence herbicidal activity index used in Table I is as follows:

| Plant Response | Index |
| --- | --- |
| Less than 25% inhibition. | 0 |
| 25 to less than 50% inhibition | 1 |
| 50 to less than 75% inhibition | 2 |
| 75 to 99% inhibition | 3 |
| 100% inhibition | 4 |

The plant species utilized in these tests are identified by letter in accordance with the following legend.

A—Canada Thistle*
B—Cocklebur
C—Velvetleaf
D—Morningglory
E—Lambsquarters, Common
F—Smartweed, Pa.
G—Yellow Nutsedge*
H—Quackgrass*
I—Johnsongrass*
J—Downy Brome
K—Barnyardgrass
*Established from vegetative propagules.

TABLE I

| Compound of Example No. | Kg/ha | Plant Species | | | | | | | | | | |
| --- | --- | --- | --- | --- | --- | --- | --- | --- | --- | --- | --- | --- |
| | | A | B | C | D | E | F | G | H | I | J | K |
| 2 | 11.2 | N | 2 | 1 | 1 | 4 | 1 | 1 | 3 | 3 | 2 | 3 |
| | 5.6 | N | 1 | 1 | 1 | 3 | 0 | 1 | 1 | 3 | 2 | 3 |
| 3 | 11.2 | N | 3 | 2 | 2 | 3 | 1 | 2 | 2 | 2 | 2 | 4 |
| | 5.6 | N | 2 | 1 | 1 | 3 | 0 | 1 | 2 | 2 | 2 | 3 |
| 4 | 11.2 | N | 1 | 1 | 1 | 3 | 1 | 1 | 1 | 2 | 1 | 3 |
| | 5.6 | N | 2 | 1 | 1 | 3 | 1 | 1 | 3 | 2 | 1 | 3 |
| 5 | 11.2 | N | 3 | 1 | 2 | 3 | 0 | 1 | 3 | 3 | 3 | 3 |
| | 5.6 | N | 3 | 1 | 1 | 3 | 0 | 1 | 1 | 2 | 2 | 3 |
| 6 | 11.2 | N | 3 | 3 | 2 | 4 | 1 | 2 | 3 | 4 | 3 | 4 |
| | 5.6 | N | 2 | 2 | 1 | 4 | 1 | 2 | 2 | 1 | 2 | 3 |

From the test results presented in Table I, it can be seen that the post-emergent herbicidal activity of the compounds of this invention is, for the most part, general in nature. In certain specific instances, however, some selectivity is demonstrated. In this regard it should be recognized that each individual species selected from the above tests is a representative member of a recognized family of plant species.

The herbicidal compositions, including concentrates which require dilution prior to application to the plants of this invention contain from 5 to 95 parts by weight of at least one compound of this invention and from 5 to 95 parts by weight of an adjuvant in liquid or solid form, for example, from about 0.25 to 25 parts by weight of wetting agent, from about 0.25 to 25 parts by weight of a dispersant and from 4.5 to about 94.5 parts by weight of inert liquid extender, e.g., water, acetone, tetrahydrofuran, all parts being by weight of the total composition. Preferably, the compositions of this invention contain from 5 to 75 parts by weight of at least one compound of this invention, together with the adjuvants. Where required, from about 0.1 to 2.0 parts by weight of the inert liquid extender can be replaced by a corrosion inhibitor such as ethanol mercaptan, sodium thiosulfate, dodecylmono or dimercaptan or anti-foaming agent such as a dimethylpolysiloxane, or both. The compositions are prepared by admixing the active ingredient with an adjuvant including diluents, extenders, carriers and conditioning agents to provide compositions in the form of finely-divided particulate solids, pellets, solutions, dispersions or emulsions. Thus, the active ingredient can be used with an adjuvant such as a finely-divided solid, a liquid of organic origin, water, a wetting agent, a dispersing agent, an emulsifying agent or any suitable combination of these.

The herbicidal compositions of this invention, particularly liquids and soluble powders, preferably contain as a conditioning agent one or more surface-active agents in amounts sufficient to render a given composition readily dispersible in water or in oil. The incorporation of a surface-active agent into the compositions greatly enhances their efficacy. By the term "surface-active agent", it is understood that wetting agents, dispersing agents, suspending agents and emulsifying agents are included therein. Anionic, cationic and non-ionic agents can be used with equal facility.

Preferred wetting agents are alkyl benzene and alkyl naphthalene sulfonates, sulfated fatty alcohols, amines or acid amides, long chain acid esters of sodium isothionate, esters of sodium sulfosuccinate, sulfated or sulfonated fatty acid esters petroleum sulfonates, sulfonated vegetable oils, polyoxyethylene derivatives of phenols and alkylphenols (particularly isooctylphenol and nonylphenol) and polyoxyethylene derivatives of the mono-higher fatty acid esters of nexitol anhydrides (e.g., sorbitan). Preferred dispersants are methyl cellulose, polyvinyl alcohol, sodium lignin, sulfonates, polymeric alkyl naphthalene sulfonates, sodium naphthalene sulfonate, polymethylene bisnaphthalenesulfonate and sodium N-methyl-N-(long chain acid) taurates.

When operating in accordance with the present invention, effective amounts of the compounds or compositions of this invention are applied to the plants, or are incorporated into aquatic media in any convenient fashion. The application of liquid and particulate solid compositions to plants or soil can be carried out by conventional methods, e.g., power dusters, boom and hand sprayers and spray dusters. The compositions can also be applied from airplanes as a dust or a spray because of their effectiveness at low dosages. The application of herbicidal compositions to aquatic plants is usually carried out by adding the compositions to the aquatic media in the area where control of the aquatic plants is desired.

The application of an effective amount of the compounds or compositions of this invention to the plant is essential and critical for the practice of the present invention. The exact amount of active ingredient to be employed is dependent upon the response desired in the plant as well as such other factors as the plant species and stage of development thereof, and the amount of rainfall as well as the specific glycine employed. In foliar treatment for the control of vegetative growth, the active ingredients are applied in amounts from about 11.2 to about 56.0 or more kilograms per hectare. In applications for the control of aquatic plants, the active ingredients are applied in amounts of from about 100 parts per million to about 1000 parts per million, based on the aquatic medium. An effective amount for phytotoxic or herbicidal control is that amount necessary for overall or selective control, i.e., a phytotoxic or herbicidal amount. It is believed that one skilled in the art can readily determine from the teachings of this specification, including examples, the approximate application rate.

There are several possible methods for applying liquid compositions of this invention to emerged plants. Such methods include the use of wiper systems whereby the plant to be treated is contacted with an absorbent material containing the particular liquid composition, a portion of which is thereby released onto the plant upon contact therewith. Such wiper systems typically comprise a reservoir of the liquid composition into which a portion of the absorbent material is placed and is fed therethrough. Generally, substances employable as absorbent material include substances of any shape or form capable of absorbing the liquid composition and releasing a portion of the same upon contact with the plant. Typical absorbent materials include felt, foam rubber, cellulose, nylon, sponges, hemp, cotton, burlap, polyester over acrylic, combinations thereof and the like. Forms of absorbent material include rope, twine, string, cloths, carpets, combinations thereof and the like. These forms may be assembled in any manner desired including a pipe rope wick, a wedge rope wick, a multi-rope wick and the like.

In another possible application method, liquid compositions may be selectively applied to weeds by the use of recirculating sprayer systems wherein the recirculating spray unit is mounted on a tractor or high clearance mobile equipment and the spray is directed horizontally onto the weeds growing over a crop. Spray not intercepted by the weeds is collected in a recovery chamber before contacting the crop and is reused. Roller applications may also be employed to apply liquid compositions to weeds growing over a crop.

In yet another possible application method, shielded applicators may be employed to direct the liquid composition in the form of a spray onto the weeds while effectively shielding the crops from the spray.

These and other possible application methods for selectively applying liquid compositions to weeds are discussed in detail in Innovative Methods of Post-Emergence Weed Control, McWhorter C. G., Southern Weed Science Society, 33rd Annual Meeting Proceedings, Jan. 15–17, 1980; Auburn University Printing Service, Auburn, Ala., U.S.A., the teachings of which are incorporated herein by reference in their entirety.

Another possible method of applying liquid compositions of this invention to plants includes controlled droplet application which is also known as the ultra low-volume chemical application. Controlled droplet application involves the production of uniform or nearly uniform spray drops of a predetermined size and the conveyance of these drops with negligible evaporation to a spray target. In particular, this method comprises feeding spray solutions to a rotary atomizer comprising a small disk with serrated edges that disperses liquid into droplets as the disk spins. Different droplet sizes are produced by changing solution flow rates to the spinning disk or changing the speed of rotation of the disk.

Those of skill in the art will recognize that the physical and chemical characteristics of the compound or composition employed will determine to a large extent the particular application method selected therewith.

The aforementioned and other methods for applying liquid compositions to plants are discussed in detail in "Rope Wick Applicator-Tool With A Future", Dale, James E., pp. 3-4, "The Recirculating Sprayer and Roundup ® Herbicide", Derting, Claude W., pp. 5-7, and "C.D.A. Herbicide Application", McGarvey, Frank X., Weeds Today, Volume 11, Number 2, pp. 8-9, Late Spring, 1980, 309 W. Clark St., Champaign, Ill., the teaching of which are incorporated herein by reference in their entirety.

Although this invention has been described with respect to specific modifications, the details thereof are not to be construed as limitations, for it will be apparent that various equivalents, changes, and modifications may be resorted to without departing from the spirit and scope thereof and it is understood that such equivalent embodiments are intended to be included herein.

What is claimed is:

1. A compound represented by the formula

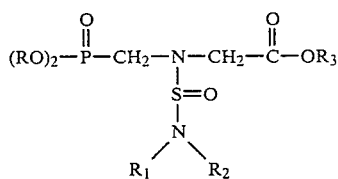

wherein R is selected from the group consisting of phenyl, or phenyl substituted with from 1 to 3 substituents independently selected from the group consisting of lower alkyl, lower alkoxy, trifluoromethyl, nitro and halogen; and wherein $R_1$ and $R_2$ are independently selected from the group consisting of alkyl, cycloalkyl, alkenyl, alkynyl, aralkyl and R; or $R_1$ and $R_2$ are independently selected from the aforerecited groups and joined together through nitrogen to form a cyclic structure having 4-8 atoms; and $R_3$ is lower alkyl or aralower alkyl.

2. A compound of claim 1 wherein R is phenyl.

3. A compound of claim 2 wherein $R_1$ and $R_2$ are the same.

4. A compound of claim 3 wherein said compound is glycine, N-[(diallylamino)sulfinyl]-N-[(diphenoxyphosphinyl)methyl]-, phenylmethyl, ester.

5. A compound of claim 3 wherein said compound is glycine, N-[(dicyclohexylamino)sulfinyl]-N-[(diphenoxyphosphinyl)methyl]-, phenylmethyl ester.

6. A compound of claim 2 wherein $R_1$ and $R_2$ are joined together to form a cyclic arrangement having 4-8 atoms therein.

7. A compond of claim 6 wherein said compound is glycine N-[(4-morpholino)sulfinyl]-N-[(diphenoxyphosphinyl)methyl]-, phenylmethyl ester.

8. A compound of claim 2 wherein $R_1$ and $R_2$ are not the same.

9. A compound of claim 8 wherein said compound is glycine, N-{[(N-methyl-N-phenyl)amino]-sulfinyl}-N-[(diphenoxyphosphinyl)methyl]-, phenylmethyl ester.

10. A compound of claim 8 wherein said compound is glycine, N-{[(N-methyl-N-benzyl)amino]-sulfinyl}-N-[(diphenoxyphosphinyl)methyl]-, methyl ester.

11. A herbicidal composition comprising an adjuvant and a herbicidally effective amount of a compound represented by the formula

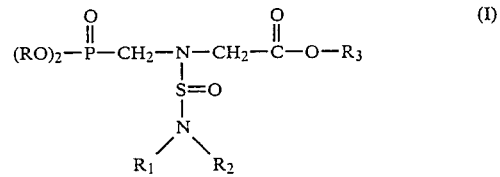

wherein R is selected from the group consisting of phenyl, or phenyl substituted with from 1 to 3 substituents independently selected from the group consisting of lower alkyl, lower alkoxy, trifluoromethyl, nitro and halogen; and wherein $R_1$ and $R_2$ are independently selected from the group consisting of alkyl, cycloalkyl, alkenyl, alkynyl, aralkyl and R; or $R_1$ and $R_2$ are independently selected from the aforerecited groups and joined together through nitrogen to form a cyclic structure having 4-8 atoms; and $R_3$ is lower alkyl or aralower alkyl.

12. A composition of claim 11 wherein R is phenyl.

13. A composition of claim 12 wherein $R_1$ and $R_2$ are the same.

14. A composition of claim 13 wherein said compound is glycine, N-[(diallylamino)sulfinyl]-N-[(diphenoxyphosphinyl)methyl]-, phenylmethyl ester.

15. A composition of claim 13 wherein said compound is glycine, N-[(dicyclohexylamino)sulfinyl]-N-[(diphenoxyphosphinyl)methyl]-, phenylmethyl ester.

16. A composition of claim 11 wherein $R_1$ and $R_2$ are joined together to form a cyclic arrangement having 4-8 atoms therein.

17. A composition of claim 16 wherein said compound is glycine, N-[(4-morpholino)sulfinyl]-N-[(diphenoxyphosphinyl)methyl]-, phenylmethyl ester.

18. A composition of claim 11 wherein $R_1$ and $R_2$ are not the same.

19. A composition of claim 18 wherein said compound is glycine, N-{[(N-methyl-N-phenyl)amino]-sulfinyl}-N-[(diphenoxyphosphinyl)methyl]-, phenylmethyl ester.

20. A composition of claim 18 wherein said compound is glycine, N-{[(N-methyl-N-benzyl)amino]-sulfinyl}-N-[(diphenoxyphosphinyl)-methyl]-, methyl ester.

21. A method of controlling undesired plants which comprises applying to said plants a herbicidally effective amount of a compound of the formula

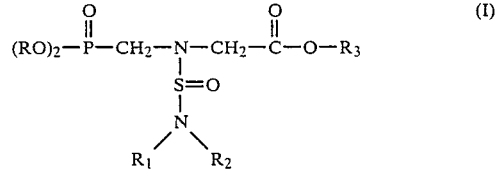

wherein R is selected from the group consisting of phenyl, or phenyl substituted with from 1 to 3 substituents independently selected from the group consisting of lower alkyl, lower alkoxy, trifluoromethyl, nitro and halogen; and wherein $R_1$ and $R_2$ are independently selected from the group consisting of alkyl, cycloalkyl, alkenyl, alkynyl aralkyl and R; or $R_1$ and $R_2$ are independently selected from the aforerecited groups and joined together through nitrogen to form a cyclic structure having 4-8 atoms; and $R_3$ is lower alkyl or aralower alkyl.

22. A method of claim 21 wherein R is phenyl.

23. A method of claim 21 wherein $R_1$ and $R_2$ are the same.

24. A method of claim 23 wherein said compound is glycine, N-[(diallylamino)sulfinyl]-N-[(diphenoxyphosphinyl)methyl]-, phenylmethyl ester.

25. A method of claim 23 wherein said compound is glycine, N-[(dicyclohexylamino)sulfinyl]-N-[(diphenoxyphosphinyl)methyl]-, phenylmethyl ester.

26. A method of claim 21 wherein $R_1$ and $R_2$ are joined together to form a cyclic arrangement having 4-8 atoms therein.

27. A method of claim 26 wherein said compound is glycine, N-[(4-morpholino)sulfinyl]-N-[(diphenoxyphosphinyl)methyl]-, phenylmethyl ester.

28. A method of claim 21 wherein $R_1$ and $R_2$ are not the same.

29. A method of claim 28 wherein said compound is glycine, N-{[(N-methyl-N-phenyl)amino]-sulfinyl}-N-[(diphenoxyphosphinyl)methyl]-, phenylmethyl ester.

30. A method of claim 28 wherein said compound is glycine, N-{[(N-methyl-N-benzyl)amino]-sulfinyl}-N-[(diphenoxyphosphinyl)methyl]-, methyl ester.

* * * * *